United States Patent
Onogi et al.

(10) Patent No.: US 9,631,999 B2
(45) Date of Patent: Apr. 25, 2017

(54) $NO_x$ DETECTION APPARATUS AND $NO_x$ SENSOR SYSTEM

(71) Applicant: NGK SPARK PLUG CO., LTD., Nagoya, Aichi (JP)

(72) Inventors: Hirotaka Onogi, Kakamigahara (JP); Kenji Kato, Nagoya (JP); Satoshi Teramoto, Nissin (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 587 days.

(21) Appl. No.: 14/080,494

(22) Filed: Nov. 14, 2013

(65) Prior Publication Data
US 2014/0136136 A1 May 15, 2014

(30) Foreign Application Priority Data

Nov. 15, 2012 (JP) .................. 2012-251343

(51) Int. Cl.
*G01L 27/00* (2006.01)
*G01N 27/417* (2006.01)

(52) U.S. Cl.
CPC ........ *G01L 27/005* (2013.01); *G01N 27/4175* (2013.01)

(58) Field of Classification Search
CPC .... G01L 27/005; G01K 3/04; G01N 27/4175; G01N 33/0006; G01N 27/4074;
(Continued)

(56) References Cited

U.S. PATENT DOCUMENTS 5,763,763 A * 6/1998 Kato .................. G01N 27/4074
204/412
5,942,190 A * 8/1999 Kato .................. G01N 27/4074
204/425
(Continued)

FOREIGN PATENT DOCUMENTS

JP 2009-210450 A 9/2009

*Primary Examiner* — Mohamed Charioui
*Assistant Examiner* — Leonard S Liang
(74) *Attorney, Agent, or Firm* — Stites & Harbison, PLLC; Jeffrey A. Haeberlin; James R. Hayne

(57) ABSTRACT

An $NO_x$ detection apparatus computes a first $NO_x$ concentration $NO_{xpo}$ on the basis of a second pumping current Ip2, and sets correction coefficients a, b (concentration variation correction information) on the basis of the first $NO_x$ concentration $NO_{xpo}$. Therefore, the $NO_x$ detection apparatus can set the correction coefficients a, b in accordance with the concentration of $NO_x$ actually contained in a to-be-measured gas. Since the $NO_x$ detection apparatus uses Equation 3, determined by the correction coefficients a, b, for correction of the first $NO_x$ concentration $NO_{xpo}$, the $NO_x$ detection apparatus can correct the first $NO_x$ concentration $NO_{xpo}$ in accordance with the state of change of the $NO_x$ concentration even when the magnitude of an output variation caused by a pressure change changes depending on the $NO_x$ concentration.

4 Claims, 10 Drawing Sheets

(58) Field of Classification Search
CPC .. G01N 27/407; G01N 27/417; G01N 27/419; G01N 27/4071; G01N 27/4067; G01N 27/4077; G01N 27/4075; G01N 27/7077; G01N 27/4065; G01N 27/4166; G01N 27/404; G01N 27/30; G01N 27/28; G01N 27/4045; G01N 27/403
USPC .............. 72/23.31; 702/98; 204/153.14, 406, 204/408–412, 424–429; 205/781, 785
See application file for complete search history.

(56) References Cited

U.S. PATENT DOCUMENTS

| | | | | |
|---|---|---|---|---|
| 6,045,673 A * | 4/2000 | Kato | ............. | G01N 27/419 204/425 |
| 6,071,393 A * | 6/2000 | Oshima | ............. | G01N 27/419 204/425 |
| 6,284,112 B1 * | 9/2001 | Kato | ............. | G01N 27/419 204/425 |
| 6,303,011 B1 * | 10/2001 | Gao | ............. | G01N 27/4074 204/425 |
| 6,442,998 B2 * | 9/2002 | Kurokawa | ............. | 204/410 |
| 7,438,791 B2 * | 10/2008 | Sakayanagi | ............. | G01N 27/4074 204/424 |
| 7,875,165 B2 * | 1/2011 | Nakasone | ............. | G01N 27/4175 204/406 |
| 8,012,325 B2 * | 9/2011 | Oya | ............. | G01N 27/419 204/424 |
| 8,398,836 B2 * | 3/2013 | Horisaka | ............. | G01N 27/4071 204/424 |
| 2003/0201172 A1 * | 10/2003 | Nakagaki | ............. | G01N 33/0037 204/290.01 |
| 2004/0231985 A1 * | 11/2004 | Kato | ............. | G01N 27/4072 204/426 |
| 2005/0211554 A1 * | 9/2005 | Kurachi | ............. | G01N 27/419 204/426 |
| 2008/0105545 A1 * | 5/2008 | Nakagaki | ............. | G01N 27/419 204/424 |
| 2009/0223820 A1 | 9/2009 | Ishiguro et al. | | |
| 2009/0242427 A1 * | 10/2009 | Muroguchi | ............. | G01N 27/419 205/781 |
| 2010/0180665 A1 * | 7/2010 | Abe | ............. | G01N 27/4065 73/23.31 |
| 2012/0199478 A1 * | 8/2012 | Sasaki | ............. | G01N 27/4065 204/406 |

* cited by examiner

| Rank | NOx pressure correction coefficient ($K_1$) |
|---|---|
| 0 | 10 |
| 1 | 14 |
| 2 | 18 |
| 3 | 22 |
| 4 | 26 |
| 5 | 30 |
| 6 | 34 |
| 7 | 38 |

FIG. 2

$NO_x$ DETECTION APPARATUS AND $NO_x$ SENSOR SYSTEM

CROSS REFERENCE TO RELATED APPLICATIONS

The present application claims priority from Japanese Patent Application No. 2012-251343, which was filed on Nov. 15, 2012, the disclosure of which is herein incorporated by reference in its entirety.

BACKGROUND OF THE INVENTION

Field of the Invention

The present invention relates to an $NO_x$ detection apparatus connected to an $NO_x$ sensor which detects the concentration of $NO_x$ contained in a to-be-measured gas, and to an $NO_x$ sensor system.

Description of Related Art

A conventionally known $NO_x$ detection apparatus is connected to an $NO_x$ sensor configured by use of a solid electrolyte member, and is used to detect the concentration of $NO_x$ contained in a to-be-measured gas.

In such an $NO_x$ sensor, the to-be-measured gas is introduced into a first measurement chamber through a predetermined diffusion resistor, and the oxygen concentration of the to-be-measured gas is adjusted to a predetermined concentration by means of a first pumping cell which is composed of a solid electrolyte member and a pair of first electrodes. Next, the to-be-measured gas having the adjusted oxygen concentration flows from the first measurement chamber into an $NO_x$ measurement chamber, and $NO_x$ contained in the to-be-measured gas is decomposed by means of a second pumping cell composed of a solid electrolyte member and a pair of second electrodes, whereby a second pumping current corresponding to the $NO_x$ concentration flows between the pair of second electrodes.

The $NO_x$ detection apparatus detects the concentration of $NO_x$ contained in the to-be-measured gas on the basis of the second pumping current output from the $NO_x$ sensor. Notably, in such an $NO_x$ sensor, which measures the gas concentration ($NO_x$ concentration) on the basis of an output (second pumping current) obtained via a pair of electrodes of the cell, the amount of the gas flowing into measurement chambers (the first measurement chamber and the $NO_x$ measurement chamber) is limited (controlled) by a predetermined diffusion resistor, whereby measurement is stabilized.

However, the conventional $NO_x$ detection apparatus has a problem in that the amount of the gas which flows into the measurement chamber changes in accordance with a change in the pressure of the to-be-measured gas in the vicinity of the attached $NO_x$ sensor, and the sensor output changes with the change in the pressure of the to-be-measured gas even when the gas concentration remains unchanged, and so the measured gas concentration involves an error.

Further, the $NO_x$ sensor has a problem in that the state of variation in the sensor output (output variation state) attributable to a change in the pressure of the to-be-measured gas differs among individual $NO_x$ sensors when the magnitude of the diffusion resistance for introducing the to-be-measured gas into the measurement chamber varies among the individual $NO_x$ sensors due to production variation, etc. of the individual $NO_x$ sensors.

To solve the above-described problem, there has been proposed a technique for suppressing a decrease in gas detection accuracy by means of setting pressure correction information in advance in accordance with the individual difference (individual characteristic) of each sensor and correcting the $NO_x$ concentration by use of the pressure correction information (see Patent Document 1). For example, the $NO_x$ concentration is corrected by use of, as the pressure correction information, Equation 2 which will be described later.

RELATED ART DOCUMENTS

Patent Document 1 is Japanese Patent Application No. 2009-210450

BRIEF SUMMARY OF THE INVENTION

However, even in the case where a single $NO_x$ sensor is used, the magnitude of an output variation caused by a change in pressure may change depending on the $NO_x$ concentration of a to-be-measured gas. In such a case, although the correction of $NO_x$ concentration performed by use of the above-mentioned pressure correction information can suppress a decrease in gas detection accuracy in a certain range of $NO_x$ concentration, the correction may fail to sufficiently suppress a decrease in gas detection accuracy in a concentration range other than the certain concentration range (may fail to suppress a decrease in gas detection accuracy over the entire concentration range.

FIG. 8 shows the results of detection of concentration of $NO_x$ (90 ppm; only NO gas was used in this evaluation) performed through use of a conventional $NO_x$ detection apparatus in a state in which "pressure correction was not preformed" and in a state in which "pressure correction was performed." FIG. 9 shows the results of detection of concentration of $NO_x$ (1500 ppm; only NO gas was used in this evaluation) performed through use of the conventional $NO_x$ detection apparatus in a state in which "pressure correction was not preformed" and in a state in which "pressure correction was performed."

As shown in FIG. 8, in the case where the $NO_x$ concentration is 90 ppm and pressure correction is not preformed, the result of detection of the $NO_x$ concentration varies with a change in pressure. In contrast, in the case where "pressure correction is performed" by use of pressure correction information, the result of detection of the $NO_x$ concentration becomes approximately 90 ppm irrespective of a change in pressure. This demonstrates that a decrease in gas detection accuracy can be suppressed.

Meanwhile, as shown in FIG. 9, in the case where the $NO_x$ concentration is 1500 ppm, gas detection accuracy decreases even when pressure correction is performed by use of pressure correction information. Specifically, in a pressure region where the pressure of the to-be measured gas is 110 kPa or lower, the result of detection of the $NO_x$ concentration falls within a range of 1450 ppm to 1550 ppm, and the error from the actual $NO_x$ concentration (1500 ppm) is small. Therefore, the effect of the correction performed by use of pressure correction information is observed. However, in a pressure region where the pressure of the to-be measured gas is 110 kPa or higher, the result of detection of the $NO_x$ concentration with pressure correction performed greatly deviates from the actual $NO_x$ concentration (1500 ppm). Therefore, even in the case where correction is performed by use of pressure correction information, gas detection accuracy decreases.

As described above, even in the case where a single $NO_x$ sensor is used, the magnitude of an output variation caused by a change in pressure may change depending on the $NO_x$ concentration of a to-be-measured gas. In such a case, although the conventional correction performed on the basis of pressure correction information can properly correct the $NO_x$ concentration in a certain concentration range, the conventional correction may fail to properly correct the $NO_x$ concentration in a concentration range other than the "certain concentration range" and may fail to suppress a decrease in gas detection accuracy over the entire concentration range.

The present invention has been accomplished in order to solve the above-described problem, and its object is to provide an $NO_x$ detection apparatus and an $NO_x$ sensor system which can suppress a decrease in the accuracy in detecting the concentration of $NO_x$ over the entire concentration range, even in the case where the magnitude of an output variation caused by a change in pressure changes depending on the $NO_x$ concentration.

In order to achieve the above-described object, the present invention provides the following means.

An $NO_x$ detection apparatus of the present invention is connected to an $NO_x$ sensor, and is adapted to detect an $NO_x$ concentration within a to-be-measured gas. The $NO_x$ sensor includes a first pumping cell which has (includes) paired first electrodes provided (positioned) internally and externally, respectively, of a first measurement chamber and which pumps out oxygen from the to-be-measured gas introduced into the first measurement chamber and pumps oxygen into the first measurement chamber to thereby adjust the concentration of oxygen within the first measurement chamber (i.e., transforms the to-be-measured gas into an oxygen-concentration-adjusted to-be-measured gas). The $NO_x$ sensor also includes a second pumping cell which has (includes) paired second electrodes provided (positioned) internally and externally, respectively, of an $NO_x$ measurement chamber communicating with the first measurement chamber and which is configured such that a second pumping current flows between the paired second electrodes. The second current corresponds to the $NO_x$ concentration within the to-be-measured gas whose oxygen concentration has been adjusted in the first measurement chamber (i.e., the oxygen-concentration-adjusted to-be-measured gas). The $NO_x$ detection apparatus comprises first concentration computation means for computing a first $NO_x$ concentration on the basis of the second pumping current; correction information setting means for setting, by using the first $NO_x$ concentration, concentration variation correction information for determining a degree of correction of the first $NO_x$ concentration; and corrective computation means for calculating the $NO_x$ concentration by correcting the first $NO_x$ concentration on the basis of the concentration variation correction information and to-be-measured gas pressure information which is input externally (i.e., the corrective computation means is also for receiving, via an external input, the to-be-measured gas pressure information).

In this $NO_x$ detection apparatus, the first $NO_x$ concentration is computed on the basis of the second pumping current, and the concentration variation correction information is set by using the first $NO_x$ concentration. Therefore, the concentration variation correction information can be set in accordance with the concentration of $NO_x$ actually contained in the to-be-measured gas.

Since this $NO_x$ detection apparatus uses the concentration variation correction information in addition to the to-be-measured gas pressure information in order to correct the first $NO_x$ concentration, the $NO_x$ detection apparatus can correct the first $NO_x$ concentration in accordance with the state of change of the concentration of $NO_x$ actually contained in the to-be-measured gas even in the case where the magnitude of an output variation caused by a pressure change changes depending on the $NO_x$ concentration.

That is, by performing such correction, the $NO_x$ detection apparatus can reduce the influence of an output variation caused by a change in the pressure of the to-be-measured gas over the entire concentration range, even in the case where the magnitude of an output variation caused by a pressure change changes depending on the $NO_x$ concentration.

Therefore, according to the $NO_x$ detection apparatus of the present invention, even in the case where the magnitude of an output variation caused by a pressure change changes depending on the $NO_x$ concentration, the influence of an output variation caused by a change in the pressure of the to-be-measured gas over the entire concentration range can be reduced, whereby a decrease in gas detection accuracy can be suppressed.

Notably, the corrective computation means may correct the first $NO_x$ concentration by using a map or a calculation formula which is determined in advance. For example, in the present invention, the corrective computation means may be configured such that it corrects the first $NO_x$ concentration by using an n-th order function regarding the to-be-measured gas pressure information, wherein the n-th order function is a quadratic function or a higher-order function, and the concentration variation correction information represents coefficients of the terms of the n-th order function.

That is, by using an n-th order function regarding the to-be-measured gas pressure information, the $NO_x$ detection apparatus can correct the first $NO_x$ concentration in accordance with the state of change of the pressure of the to-be-measured gas. Also, since the coefficients of the terms of the n-th order function which serve as the concentration variation correction information are set by the correction information setting means on the basis of the first $NO_x$ concentration, the coefficients of the terms of the n-th order function can be changed in accordance with the concentration of $NO_x$ actually contained in the to-be-measured gas.

Therefore, by performing such correction, the $NO_x$ detection apparatus of the present invention can reduce the influence of an output variation caused by a change in the pressure of the to-be-measured gas over the entire concentration range, to thereby suppress a decrease in gas detection accuracy, even in the case where the magnitude of an output variation caused by a pressure change changes depending on the $NO_x$ concentration.

The first concentration computation means may be configured to compute a second $NO_x$ concentration on the basis of the second pumping current, and obtain the first $NO_x$ concentration by correcting the second $NO_x$ concentration on the basis of pressure variation correction information which is individually set for each of $NO_x$ sensors in advance (i.e., the first concentration computation means obtains the first $NO_x$ concentration by correcting the second $NO_x$ concentration on the basis of predetermined pressure variation correction information of the $NO_x$ sensor).

By setting the pressure variation correction information in accordance with the individual difference of each sensor (the characteristic of each sensor), correcting the second $NO_x$ concentration by using the pressure variation correction information, and using the corrected second $NO_x$ concentration as the first $NO_x$ concentration, the $NO_x$ detection apparatus can set the concentration variation correction information by using the first $NO_x$ concentration in which the correction by the pressure variation correction information is reflected. As a result, the accuracy in setting the concentration variation correction information is improved, whereby a decrease in gas detection accuracy caused by a change in the pressure of the to-be-measured gas can be suppressed to a greater extent.

The $NO_x$ detection apparatus of the present invention may further comprise specific concentration determination means for determining whether or not the first $NO_x$ concentration falls within a predetermined specific concentration range; and first concentration correction means for correcting the first $NO_x$ concentration by using specific concentration correction information which is individually set for each of $NO_x$ sensors in advance (i.e., predetermined specific concentration correction information), wherein when the specific concentration determination means determines that the first $NO_x$ concentration falls within the predetermined specific concentration range, the correction information setting means sets the concentration variation correction information on the basis of the first $NO_x$ concentration corrected by the first concentration correction means, and when the specific concentration determination means determines that the first $NO_x$ concentration does not fall within the predetermined specific concentration range, the correction information setting means sets the concentration variation correction information on the basis of the first $NO_x$ concentration which is not corrected by the first concentration correction means.

That is, even in the case where an $NO_x$ sensor whose output involves an error in a specific concentration range is used, it is possible to detect the $NO_x$ concentration while reducing the influence of the error of the sensor output, because the first $NO_x$ concentration is corrected by the first concentration correction means if the first $NO_x$ concentration computed on the basis of the second pumping current falls within the specific concentration range.

When the specific concentration determination means determines that the first $NO_x$ concentration falls within the predetermined specific concentration range, the correction information setting means sets the concentration variation correction information on the basis of the first $NO_x$ concentration corrected by the first concentration correction means. Therefore, the present $NO_x$ detection apparatus can set the concentration variation correction information while reducing the influence of the error of the sensor output. Thus, the present $NO_x$ detection apparatus can detect the $NO_x$ concentration while reducing the influence of the error of the sensor output.

Therefore, according to the present invention, even in the case where an $NO_x$ sensor whose output involves an error in the specific concentration range is used, it is possible to detect the $NO_x$ concentration while reducing the influence of the error of the sensor output. Further, even in the case where the magnitude of the output variation caused by a change in pressure changes depending on the $NO_x$ concentration, it is possible to reduce the influence of the output variation caused by a change in the pressure of the to-be-measured gas, to thereby suppress a decrease in gas detection accuracy.

Notably, the specific concentration determination means may be configured to determine whether or not the first $NO_x$ concentration is higher than a predetermined specific concentration. In this case, when the specific concentration determination means determines that the first $NO_x$ concentration is higher than the predetermined specific concentration, the correction of the first $NO_x$ concentration by the concentration correction means is performed, and when the specific concentration determination means determines that the first $NO_x$ concentration is not higher than the predetermined specific concentration, the correction of the first $NO_x$ concentration by the concentration correction means is not performed.

The $NO_x$ detection apparatus having such a configuration can suppress a decrease in gas detection accuracy even in the case where the gas detection value based on the sensor output involves an error when the $NO_x$ concentration is higher than the specific concentration.

In order to achieve the above-described object, the present invention also provides an $NO_x$ sensor system which comprises an $NO_x$ sensor including a first pumping cell which has (includes) paired first electrodes provided (positioned) internally and externally, respectively, of a first measurement chamber and which pumps out oxygen from the to-be-measured gas introduced into the first measurement chamber and pumps oxygen into the first measurement chamber to thereby adjust the concentration of oxygen within the first measurement chamber (i.e., transforms the to-be-measured gas into an oxygen-concentration-adjusted to-be-measured gas); and a second pumping cell which has (includes) paired second electrodes provided (positioned) internally and externally, respectively, of an $NO_x$ measurement chamber communicating with the first measurement chamber and which is configured such that a second pumping current flows between the paired second electrodes. The second current corresponds to an $NO_x$ concentration within a to-be-measured gas whose oxygen concentration has been adjusted in the first measurement chamber (i.e., the oxygen-concentration-adjusted to-be-measured gas). The $NO_x$ sensor system also includes an $NO_x$ detection apparatus according to any one of the above-described embodiments which is connected to the $NO_x$ sensor and is adapted to detect the $NO_x$ concentration within the to-be-measured gas.

Since this $NO_x$ sensor system includes the $NO_x$ detection apparatus according to any one of claims 1 to 4, it provides an action and effects similar to those achieved by the above-described $NO_x$ detection apparatus.

Therefore, according to the $NO_x$ sensor system of the present invention, even in the case where the magnitude of an output variation caused by a pressure change changes depending on the $NO_x$ concentration, the influence of an output variation caused by a change in the pressure of the to-be-measured gas over the entire concentration range can be reduced, whereby a decrease in gas detection accuracy can be suppressed.

According to the present invention, even in the case where the magnitude of an output variation caused by a pressure change changes depending on the $NO_x$ concentration, the influence of an output variation caused by a change in the pressure of the to-be-measured gas over the entire concentration range can be reduced, whereby a decrease in gas detection accuracy can be suppressed.

BRIEF DESCRIPTION OF THE DRAWINGS

Illustrative aspects of the invention will be described in detail with reference to the following figures wherein:

FIG. 2 is a table representing a map for determining an $NO_x$ pressure correction coefficient ($k_1$).

DETAILED DESCRIPTION OF EXEMPLARY EMBODIMENTS OF THE INVENTION

Preferred embodiments of the present invention will next be described with reference to the drawings. However, the embodiments described below are mere examples of applications of the present invention. The contents of the embodiments should not be construed as limiting the invention.

1. First Embodiment 1-1. Overall Configuration

Figure 1:
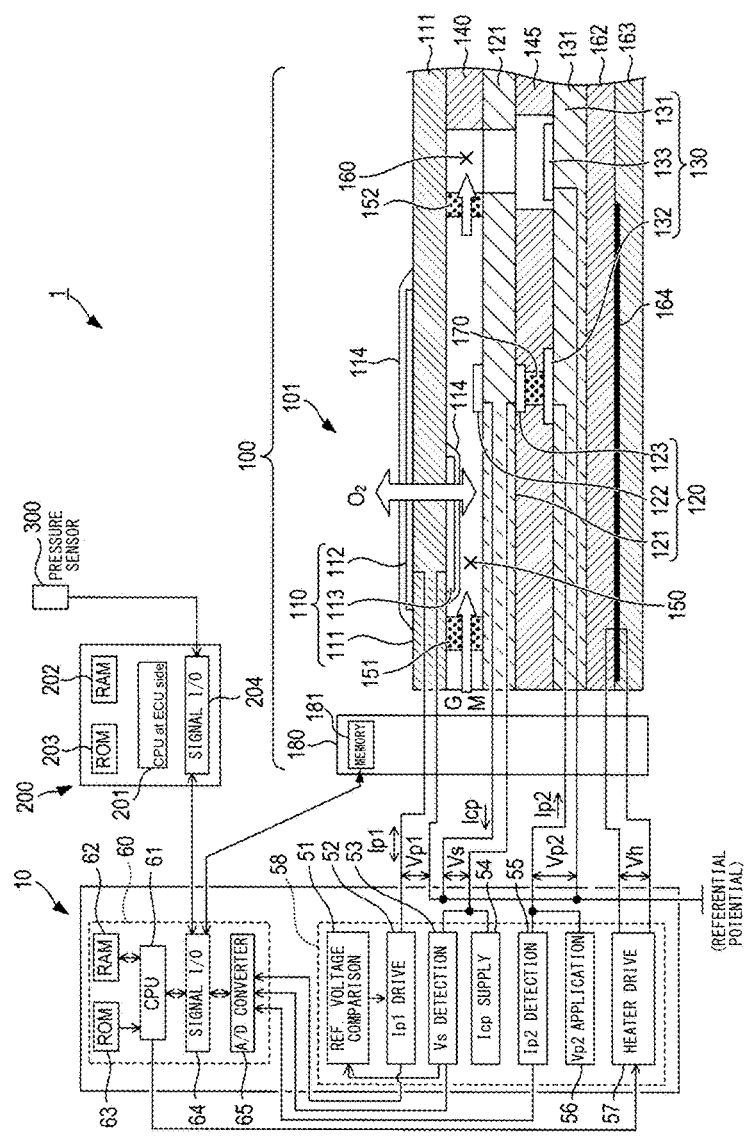
FIG. 1 is a block diagram showing the configuration of an $NO_x$ sensor control apparatus ($NO_x$ detection apparatus) according to a first embodiment of the present invention.

FIG. 1 is a block diagram showing the configuration of an $NO_x$ sensor system 1 according to a first embodiment of the present invention. This embodiment is an example in which the $NO_x$ sensor system 1 corrects an oxygen concentration equivalent value and an $NO_x$ concentration equivalent value in accordance with pressure of exhaust gas.

The $NO_x$ sensor system 1 includes at least an $NO_x$ sensor control apparatus 10 (hereinafter also referred to as an "$NO_x$ detection apparatus 10") and an $NO_x$ sensor 100.

The $NO_x$ detection apparatus 10 is mounted on a vehicle including an unillustrated internal combustion engine (hereinafter also referred to as an "engine"), and is electrically connected to a connector 180 of the $NO_x$ sensor 100. A semiconductor memory 181 (hereinafter also referred to as a "storage means 181"), such as ROM or the like, is incorporated into the connector 180 so as to store various coefficients (to be described later) set for each individual $NO_x$ sensor 100.

Further, the $NO_x$ detection apparatus 10 is electrically connected to a vehicle-side control apparatus 200 (hereinafter may be referred to as an "ECU 200"). The ECU 200 receives data representing oxygen concentration and $NO_x$ concentration within exhaust gas which have been corrected by the $NO_x$ detection apparatus 10, and executes processing for controlling the operation state of the engine, processing for removing $NO_x$ accumulated in catalyst, and other processing on the basis of the received data. Further, the ECU 200 acquires from a pressure sensor 300 information representing the pressure of exhaust gas flowing through an exhaust pipe, and sends the information to the $NO_x$ detection apparatus 10.

Notably, the method of acquiring the information representing the pressure of the exhaust gas is not limited to acquiring it from the pressure sensor 300. For example, the ECU 200 reads the rotational speed and load of the engine, and determines the pressure of the exhaust gas from these pieces of information and by use of a map or calculation equation previously stored in ROM 203.

The ECU 200 includes an ECU-side CPU (central processing unit) 201, RAM 202, ROM 203, a signal input/output section 204, and an unillustrated clock generator. Programs stored in the ROM or the like in advance are executed by the CPU.

The $NO_x$ detection apparatus 10 includes a control circuit 58 and a microcomputer 60 provided on a circuit board. The microcomputer 60, which controls the entirety of the $NO_x$ detection apparatus 10, includes a CPU (central processing unit) 61, RAM 62, ROM 63, a signal input/output section 64, an A/D converter 65, and an unillustrated clock generator. Programs stored in the ROM 63 or the like in advance are executed by the CPU.

The control circuit 58 includes a reference-voltage comparison circuit 51, an Ip1 drive circuit 52, a Vs detection circuit 53, an Icp supply circuit 54, an Ip2 detection circuit 55, a Vp2 application circuit 56, and a heater drive circuit 57. The control circuit 58 controls the $NO_x$ sensor 100, detects first and second pumping currents flowing through the $NO_x$ sensor 100, and outputs the detected first and second pumping currents to the microcomputer 60.

Next, the configuration of the $NO_x$ sensor 100 will be described. The $NO_x$ sensor 100 includes an $NO_x$ sensor element 101; a housing which accommodates the $NO_x$ sensor element 101; a connector 180 for connecting the $NO_x$ sensor element 101 and the $NO_x$ detection apparatus 10; and a lead wire connected to the $NO_x$ sensor element 101. Since the structure of the sensor itself is known, only the $NO_x$ sensor element 101 of the $NO_x$ sensor 100 will be described below with reference to a longitudinal cross sectional view of the $NO_x$ sensor element 101.

The $NO_x$ sensor element 101 has a layered structure formed by stacking a first solid electrolyte layer 111, an insulation layer 140, a second solid electrolyte layer 121, an insulation layer 145, a third solid electrolyte layer 131, and insulation layers 162 and 163 in this sequence. A first measurement chamber 150 is defined between the first solid electrolyte layer 111 and the second solid electrolyte layer 121. A to-be-measured gas GM is introduced from the outside into the first measurement chamber 150 via a first diffusion resistor 151 disposed at the inlet (the left end in FIG. 1) of the first measurement chamber 150.

A second diffusion resistor 152 is disposed at the end of the first measurement chamber 150 opposite the inlet thereof. A second measurement chamber 160 (corresponding to the "$NO_x$ measurement chamber" of the present invention) is defined on the right side of the first measurement chamber 150, and communicates therewith via the second diffusion resistor 152. The second measurement chamber 160 is formed between the first solid electrolyte layer 111 and the third solid electrolyte layer 131 such that the second measurement chamber 160 penetrates through the second solid electrolyte layer 121.

An elongated plate-shaped heater 164, which extends along the longitudinal direction of the $NO_x$ sensor element 101, is embedded between the insulation layers 162 and 163. The heater 164 is used to heat the gas sensor to an activation temperature so as to increase the oxygen-ion conductivity of the solid electrolyte layer, to thereby stabilize the operation of the gas sensor.

The insulation layers 140 and 145 are formed mainly of alumina, and the first and second diffusion resistors 151 and 152 are formed of a porous material such as alumina. Further, the heater 164 is formed of platinum or the like.

A first pumping cell 110 includes the first solid electrolyte layer 111, which is formed mainly of zirconia having oxygen-ion conductivity; and paired inside and outside first pumping electrodes 113 and 112 disposed to sandwich the first solid electrolyte layer 111. The inside first pumping electrode 113 faces the first measurement chamber 150. Each of the inside and outside first pumping electrodes 113 and 112 is formed mainly of platinum; and the surface of each electrode is covered by a protection layer 114 formed of a porous material.

An oxygen concentration detection cell 120 includes the second solid electrolyte layer 121, which is formed mainly of zirconia; and a detection electrode 122 and a reference electrode 123 disposed to sandwich the second solid electrolyte layer 121. The detection electrode 122 faces the first measurement chamber 150 at a location downstream of the inside first pumping electrode 113. Each of the detection electrodes 122 and 123 is formed mainly of platinum.

Notably, the insulation layer 145 is cut out to form a cut-out such that the reference electrode 123 in contact with the second solid electrolyte layer 121 is disposed in the cut-out; and the cut-out is filled with a porous material, whereby a reference oxygen chamber 170 is formed. A constant weak current is supplied in advance to the oxygen concentration detection cell 120 by use of the Icp supply circuit 54, whereby oxygen is fed from the first measurement chamber 150 into the reference oxygen chamber 170 so as to establish an oxygen reference.

A second pumping cell 130 includes the third solid electrolyte layer 131, which is formed mainly of zirconia; an inside second pumping electrode 133 disposed on a surface region of the third solid electrolyte layer 131, whose surface region faces the second measurement chamber 160; and a counterpart second pumping electrode 132, which forms a pair together with the inside second pumping electrode 133. Each of the inside second pumping electrode 133 and the counterpart second pumping electrode 132 is formed mainly of platinum.

Notably, the counterpart second pumping electrode 132 is disposed on the third solid electrolyte layer 131 at a location corresponding to the cut-out of the insulation layer 145, so that the counterpart second pumping electrode 132 faces the reference electrode 123 via the reference oxygen chamber 170.

The inside first pumping electrode 113, the detection electrode 122, and the inside second pumping electrode 133 are connected to a reference potential. The outside first pumping electrode 112 is connected to the Ip1 drive circuit 52, and the reference electrode 123 is connected to the Vs detection circuit 53 and the Icp supply circuit 54 in parallel. Further, the counterpart second pumping electrode 132 is connected to the Ip2 detection circuit 55 and the Vp2 application circuit 56 in parallel. The heater drive circuit 57 is connected to the heater 164.

The various circuits included in the control circuit 58 have the following functions.

The Ip1 drive circuit 52 supplies a first pumping current Ip1 between the inside first pumping electrode 113 and the outside first pumping electrode 112, while detecting the first pumping current Ip1. At that time, a voltage Vp1 is generated between the inside first pumping electrode 113 and the outside first pumping electrode 112.

The Vs detection circuit 53 detects an inter-electrode voltage Vs between the detection electrode 122 and the reference electrode 123, and outputs the detection result to the reference-voltage comparison circuit 51.

The reference-voltage comparison circuit 51 compares a reference voltage (e.g., 425 mV) and the output of the Vs detection circuit 53, and outputs a comparison result to the Ip1 drive circuit 52. The Ip1 drive circuit 52 controls the Ip1 current such that the inter-electrode voltage Vs becomes equal to the above-described reference voltage, to thereby adjust the oxygen concentration within the first measurement chamber 150 to a level at which $NO_x$ does not decompose.

The Icp supply circuit 54 causes a weak current Icp to flow between the detection electrode 122 and the reference electrode 123 so as to feed oxygen from the first measurement chamber 150 into the reference oxygen chamber 170, to thereby expose the reference electrode 123 to a predetermined oxygen concentration, which serves as a reference.

The Vp2 application circuit 56 applies a constant voltage Vp2 (e.g., 450 mV) between the inside second pumping electrode 133 and the counterpart second pumping electrode 132, the voltage being determined such that the $NO_x$ gas within the to-be-measured gas GM is decomposed into oxygen ($O_2$) and nitrogen ($N_2$). Thus, the $NO_x$ is decomposed into nitrogen and oxygen.

The Ip2 detection circuit 55 detects a second pumping current Ip2 which flows through the second pumping cell 130 so as to pump out from the second measurement chamber 160 the oxygen produced as a result of decomposition of $NO_x$.

The Ip1 drive circuit 52 outputs the detected value of the first pumping current Ip1 to the A/D converter 65. Further, the Ip2 detection circuit 55 outputs the detected value of the second pumping current Ip2 to the A/D converter 65.

The A/D converter 65 converts these values to digital values, and outputs them to the CPU 61 via the signal input/output section 64.

Next, an example of control of the $NO_x$ sensor 100 performed by use of the control circuit 58 will be described. First, when electrical power is supplied from an external power supply upon startup of the engine, the heater 164 is activated by a heater voltage Vh applied thereto via the heater drive circuit 57 so as to heat the first pumping cell 110, the oxygen concentration detection cell 120, and the second pumping cell 130 to the activation temperature. Further, the Icp supply circuit 54 causes the weak current Icp to flow between the detection electrode 122 and the reference electrode 123. Thus, oxygen is fed from the first measurement chamber 150 into the reference oxygen chamber 170 to be used as a reference.

After completion of heating of the cells 110, 120, and 130 to the activation temperature, the first pumping cell 110 pumps out oxygen contained in the to-be-measured gas (exhaust gas) GM having flowed into the first measurement chamber 150 such that the oxygen flows from the inside first pumping electrode 113 toward the outside first pumping electrode 112.

At that time, the oxygen concentration within the first measurement chamber 150 corresponds to the inter-electrode voltage (inter-terminal voltage) Vs of the oxygen concentration detection cell 120. Therefore, the Ip1 drive circuit 52 controls the first pumping current Ip1, which flows through the first pumping cell 110, such that the inter-electrode voltage Vs becomes equal to the above-described reference voltage, to thereby adjust the oxygen concentration within the first measurement chamber 150 to a level at which $NO_x$ decomposes as little as possible.

The to-be-measured gas GM having the adjusted oxygen concentration further flows toward the second measurement chamber 160. The Vp2 application circuit 56 applies, as the inter-electrode voltage (inter-terminal voltage) of the second pumping cell 130, the constant voltage Vp2 determined such that the $NO_x$ gas within the to-be-measured gas GM is decomposed into oxygen and $N_2$ gas (a voltage (e.g., 450 mV) higher than the control voltage of the oxygen concentration detection cell 120), to thereby decompose the $NO_x$ into nitrogen and oxygen. Thus, the second pumping current Ip2 flows through the second pumping cell 130 such that the oxygen produced as a result of the decomposition of the $NO_x$ is pumped out from the second measurement chamber 160. Since a linear relation exists between the second pumping current Ip2 and the $NO_x$ concentration, the $NO_x$ concentration within the to-be-measured gas can be detected from the second pumping current Ip2 detected by the Ip2 detection circuit 55.

1-2. Pressure Correction for $NO_x$ Concentration

In the $NO_x$ detection apparatus 10 according to the first embodiment of the present invention, the pressure correction for the $NO_x$ concentration is performed in accordance with the following Equation 1.

$$Rno = NO_{xpo} \cdot \left[1 + \frac{\Delta NO}{100}\right] \quad (1)$$

Notably, Rno represents corrected $NO_x$ concentration, $NO_{xpo}$ represents a value obtained by Equation 2, and $\Delta NO$ represents a value obtained by Equation 3.

$$NO_{xpo} = NO_{xp} \cdot \left[\frac{k_1 + P}{P}\right] \cdot \left[\frac{Po}{k_1 + Po}\right] \quad (2)$$

$$\Delta NO = (a \cdot \Delta P^2 + b \cdot \Delta P) \times C \quad (3)$$

Notably, in Equation 2, $NO_{xp}$ represents $NO_x$ concentration at pressure P before pressure correction (second $NO_x$ concentration calculated from the second pumping current); $NO_{xpo}$ represents $NO_x$ concentration at pressure Po after pressure correction (first $NO_x$ concentration); P represents the pressure (kPa) of the to-be-measured gas; Po represents the atmospheric pressure (=101.3 kPa); and $k_1$ represents an $NO_x$ pressure correction coefficient ($NO_x$ pressure correction information). Correction coefficients a and b in Equation 3 are determined by the processing performed in step S16 or S20 of a pressure correction processing routine which will be described later. Notably, in Equation 3, $\Delta P$ represents a value obtained by subtracting the atmospheric pressure Po from the pressure P of the to-be-measured gas, and a constant C represents individual information which is set in advance for each $NO_x$ sensor 100 and which is stored in the semiconductor memory 181.

Notably, since the second pumping current Ip2 has a fixed relation with the $NO_x$ concentration within the to-be-measured gas, the second $NO_x$ concentration $NO_x$ at the pressure P can be calculated from the second pumping current Ip2. The microcomputer 60 performs this calculation by reading out of the ROM 63 an equation representing the relation between Ip2 and the $NO_x$ concentration within the to-be-measured gas.

The $NO_x$ pressure correction coefficient ($k_1$) is selected from a map shown in FIG. 2. A value of $k_1$ corresponding to a rank assigned to an individual $NO_x$ sensor is set as the $NO_x$ pressure correction coefficient for the $NO_x$ sensor. Notably, each $NO_x$ detection apparatus uses only one of the above-described correction ranks. In this case, before the $NO_x$ detection apparatus is shipped out, the map of FIG. 2 is previously stored in the semiconductor memory 181 of the individual $NO_x$ sensor.

Each $NO_x$ sensor is connected to an external testing device, and an $NO_x$ concentration equivalent value is calculated from the second pumping current Ip2 in a state in which a reference gas is used and the gas pressure is selectively set to a plurality of known gas pressures, whereby the value of $k_1$ is determined. For example, in the case where the $NO_x$ concentration was measured at two points, the value of $k_1$ is determined from the slope of a straight line connecting the two points. Subsequently, a rank shown in the map of FIG. 2 whose value of $k_1$ is closest to the above-mentioned value of $k_1$ determined from the slope is selected, and is used for the $NO_x$ sensor. For example, a flag indicating the rank is set in the map. Thus, only data corresponding to a single correction rank within the map is referred to. Notably, a gas containing NO (90 ppm), $H_2O$ (3%), $O_2$ (9%), and $N_2$ (balance) was used as the reference gas. In this manner, the value of $k_1$ for each individual $NO_x$ sensor is stored in the semiconductor memory 181.

Notably, in the case where the $NO_x$ concentration was measured at three or more points, the value of $k_1$ may be set as a predetermined curve or a map in which a coefficient is assigned to each of pressure ranges.

The method for pressure correction is not limited to use of functions such as Equations 1 to 3, and a map in which a correction amount is assigned to each of pressure ranges may be used.

In the $NO_x$ detection apparatus 10 according to the first embodiment of the present invention, the pressure correction for the oxygen concentration is performed in accordance with the following Equation 4, wherein $O_P$ represents an oxygen concentration at pressure P before pressure correction (oxygen concentration equivalent value calculated from the first pumping current); $O_{Po}$ represents oxygen concentration at pressure Po after pressure correction (oxygen concentration equivalent value); P represents the pressure (kPa) of the to-be-measured gas; Po represents the atmospheric pressure (=101.3 kPa); and $k_2$ represents an oxygen pressure correction coefficient (oxygen pressure correction information).

$$O_{po} = O_P \cdot \left[\frac{k_2 + P}{P}\right] \cdot \left[\frac{Po}{k_2 + Po}\right] \quad (4)$$

Notably, since the first pumping current Ip1 has a fixed relation with the oxygen concentration within the to-be-measured gas, the uncorrected oxygen concentration $O_P$ at the pressure P can be calculated from the first pumping current Ip1. Specifically, the microcomputer 60 performs this calculation by reading out of the ROM 63 an equation representing the relation between the first pumping current Ip1 and the oxygen concentration within the to-be-measured gas.

The oxygen pressure correction coefficient ($k_2$) is selected from a map similar to that shown in FIG. 2. A value of $k_2$ corresponding to a rank assigned to the individual $NO_x$ sensor is set as the oxygen pressure correction coefficient for the $NO_x$ sensor. Thus, a selected value of $k_2$ is stored in the semiconductor memory 181. Similar to the above-described $k_1$, the value of $k_2$ is determined by connecting each $NO_x$ sensor to an external testing device, and calculating an oxygen concentration equivalent value from the first pumping current Ip1 in a state in which a reference gas is used and the gas pressure is selectively set to a plurality of known gas pressures.

1-3. Pressure Correction Processing

Figure 3A:
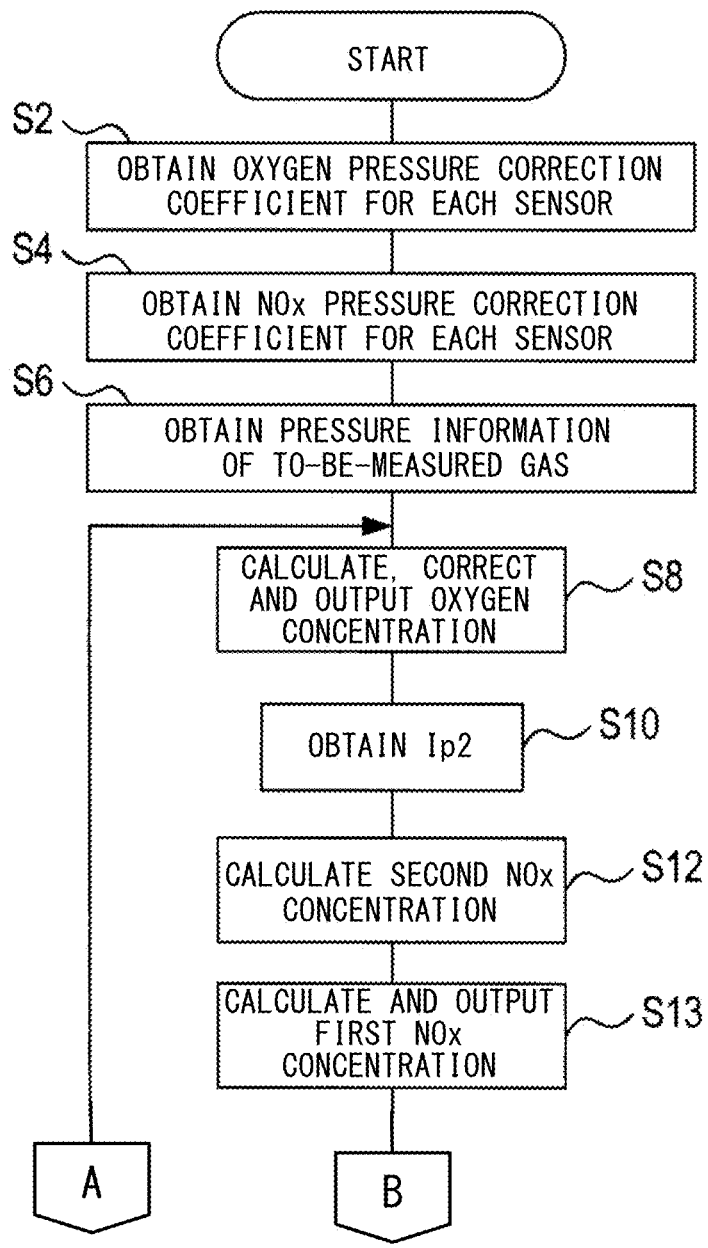
FIGS. 3A and 3B are flowcharts showing the details of pressure correction processing performed in the $NO_x$ detection apparatus.
Figure 3B:
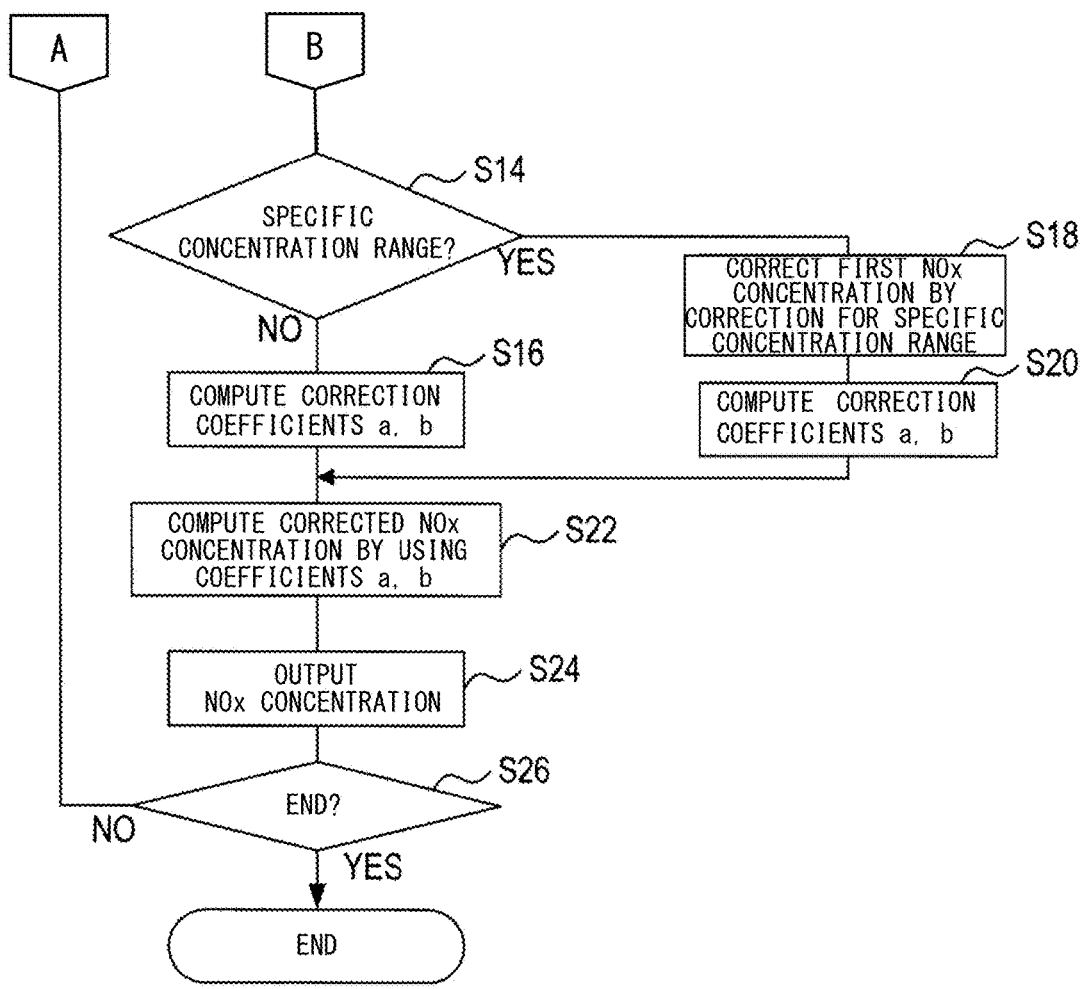

Next, pressure correction processing performed by the $NO_x$ detection apparatus 10 according to the first embodiment of the present invention will be described in detail with reference to flowcharts of FIGS. 3A and 3B. Notably, the pressure correction processing is performed by the microcomputer 60.

Upon start of the pressure correction processing, in step S2, the microcomputer 60 accesses the semiconductor memory 181 mounted on the connector 180 of the $NO_x$ sensor 100, and acquires the oxygen pressure correction coefficient ($k_2$) from the semiconductor memory 181.

In step S4 subsequent thereto, the microcomputer 60 accesses the semiconductor memory 181, and acquires the $NO_x$ pressure correction coefficient ($k_1$) from the semiconductor memory 181.

In step S6 subsequent thereto, the microcomputer 60 acquires the pressure of the to-be-measured gas (pressure information) via the ECU 200.

Next, in step S8, the microcomputer 60 calculates an oxygen concentration, corrects the calculated oxygen concentration, and outputs the corrected oxygen concentration. Specifically, in step S8, the microcomputer 60 first acquires a value of the first pumping current Ip1 from the Ip1 drive circuit 52 (in actuality, a detection signal generated through voltage conversion of the first pumping current Ip1). The microcomputer 60 then reads out of the ROM 63 an equation representing the relation between the first pumping current Ip1 and the oxygen concentration of the to-be-measured gas, and calculates the oxygen concentration before pressure correction $O_P$ (the oxygen concentration equivalent value $O_P$). Next, the microcomputer 60 applies the oxygen pressure correction coefficient and the pressure of the to-be-measured gas obtained in steps S2 and S6 to Equation 4 so as to calculate the oxygen concentration $O_{Po}$ after pressure correction. Here, $O_{Po}$ represents the oxygen concentration at the pressure Po (atmospheric pressure). The microcomputer 60 then outputs (transmits) the calculated oxygen concentration $O_{Po}$ to the ECU 200 via the signal input/output section 64.

In the subsequent step S10, the microcomputer 60 acquires a value of the second pumping current Ip2 from the Ip2 detection circuit 55 (in actuality, a detection signal generated through voltage conversion of the second pumping current Ip2).

Next, in step S12, the microcomputer 60 reads out of the ROM 63 an equation representing the relation between the second pumping current Ip2 and the $NO_x$ concentration of the to-be-measured gas, and calculates the second $NO_x$ concentration ($NO_x$ concentration at pressure P before pressure correction) $NO_{xp}$.

Next, in Step 13, the microcomputer 60 calculates the first NOx concentration NOxpo (NOx concentration at pressure Po after pressure correction), and outputs the calculation result. Specifically, in step S13, the microcomputer 60 applies to the above-described Equation 2 the second $NO_x$ concentration $NO_{xp}$ and the $NO_x$ pressure correction coefficient and the pressure of the to-be-measured gas which have been acquired in steps S4 and S6, to thereby calculate the first $NO_x$ concentration ($NO_x$ concentration after pressure correction) $NO_{xpo}$. Here, the first $NO_x$ concentration $NO_{xpo}$ is a value at the pressure Po (atmospheric pressure). The microcomputer 60 then outputs (transmits) the calculated first $NO_x$ concentration $NO_{xpo}$ to the ECU 200 via the signal input/output section 64.

Next, in step S14, the microcomputer 60 determines whether or not the first $NO_x$ concentration $NO_{xpo}$ falls in a predetermined specific concentration range. In the case where the microcomputer 60 makes an "Yes" determination, it proceeds to step S18. In the case where the microcomputer 60 makes a "No" determination, it proceeds to step S16. In the $NO_x$ detection apparatus 10 of the present embodiment, a "concentration range of 90 ppm or higher" is set as the specific concentration range.

Upon making a "No" determination in step S14, in step S16, the microcomputer 60 reads out of the semiconductor memory 181 the map data which has been prepared in advance, and calculates the correction coefficients a and b from the first $NO_x$ concentration $NO_{xpo}$ by use of the map data. The correction coefficients a and b are the coefficients in the above-described Equation 3. Equation 3 is used for correction processing performed in step S22 which will be described later.

Figure 4:
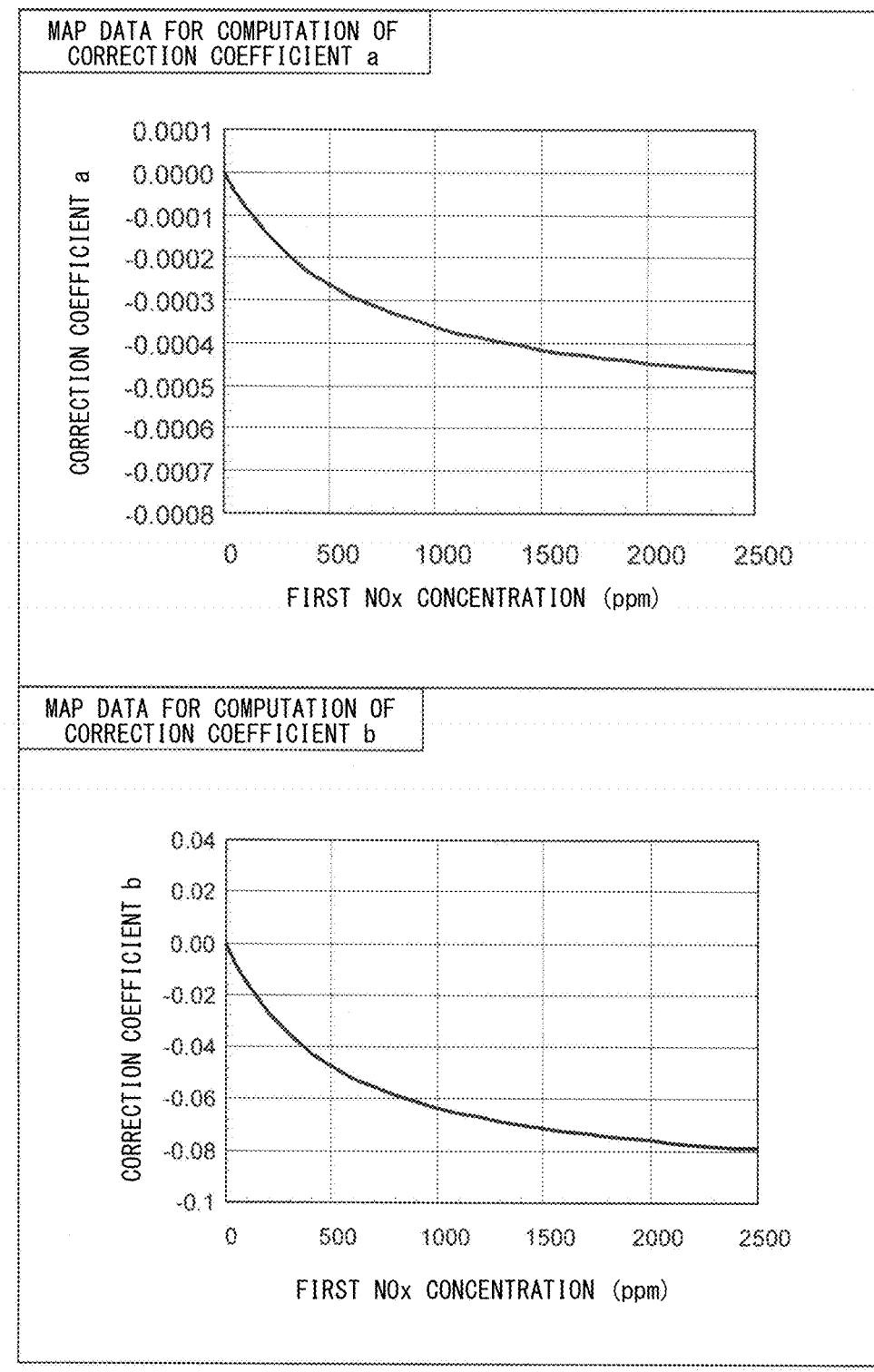
FIG. 4 consists of graphs showing example map data sets used for computing correction coefficients a and b, respectively.

FIG. 4 shows an example of the map data used in the above-described computation processing. The map data concerning the correction coefficients a and b is set in advance for each $NO_x$ sensor 100. Before the $NO_x$ detection apparatus is shipped out, the map data is stored in the semiconductor memory 181 of each $NO_x$ sensor.

Upon making an "Yes" determination in step S14, in step S18, the microcomputer 60 corrects the first $NO_x$ concentration $NO_{xpo}$ by use of an equation which is adapted for correction for the specific concentration range (hereinafter referred to as the "correction equation for specific concentration range") and which is set in advance for each $NO_x$ sensor 100. Specifically, the microcomputer 60 corrects the first $NO_x$ concentration $NO_{xpo}$ by use of the correction equation for specific concentration range, which is represented by the following Equation 5.

$$Y = \alpha \cdot x^2 + \beta \cdot x + \gamma \qquad (5)$$

Notably, in Equation 5, a variable X represents a "first $NO_x$ concentration before correction" (first $NO_x$ concentration $NO_{xpo}$), and a variable Y represents a "first $NO_x$ concentration after correction". Further, coefficients $\alpha$, $\beta$, and $\gamma$ are set in advance for each individual $NO_x$ sensor 100. Before the $NO_x$ detection apparatus is shipped out, values of the coefficients $\alpha$, $\beta$, and $\gamma$ are stored in the semiconductor memory 181 of each $NO_x$ sensor.

to an external testing device, and an $NO_x$ concentration equivalent value is calculated from the second pumping current Ip2 in a state in which a determining gas is used and the gas concentration is set to a known gas concentration, whereby a difference (output drop ratio [%]) between the value of the known gas concentration and the $NO_x$ concentration equivalent value is detected. Subsequently, values of the coefficients $\alpha$, $\beta$, and $\gamma$ are determined on the basis of the output drop ratio and the map data shown in FIG. 5.

Figure 5:
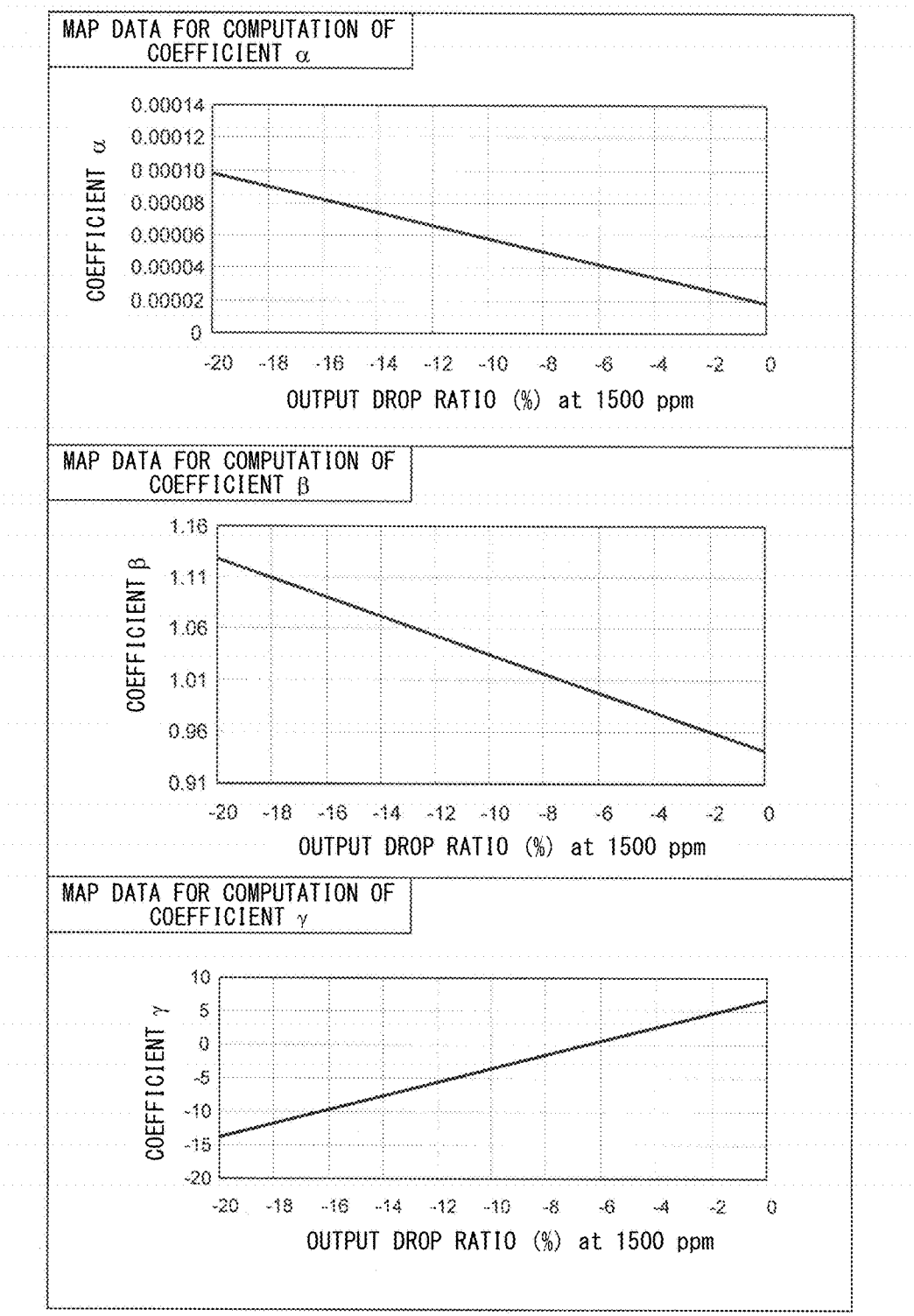
FIG. 5 consists of graphs showing example map data sets used for computing correction coefficients α, β, and γ, respectively.

Notably, the map data shown in FIG. 5 is stored in the external testing device, and the values of the coefficients $\alpha$, $\beta$, and $\gamma$ for each $NO_x$ sensor are stored in the semiconductor memory 181 in accordance with the results of detection of the output drop ratio. FIG. 5 shows an example of map data for determining the values of the coefficients $\alpha$, $\beta$, and $\gamma$ on the basis of the output drop ratio detected when a gas whose $NO_x$ concentration is 1500 ppm is used as a determining gas.

Next, in step S20, the microcomputer 60 determines the correction coefficients a and b on the basis of the first $NO_x$ concentration $NO_{xpo}$ corrected in step S18, while referring to the map data prepared in advance.

Notably, the map data used in step S20 is the same as that used in step S16.

After completion of step S16 or S20, in step S22, the microcomputer 60 corrects the first $NO_x$ concentration $NO_{xpo}$ by use of a pressure variation correction equation which is set for each $NO_x$ sensor 100 in advance. Specifically, the above-described Equation 1 is the pressure variation correction equation. The microcomputer 60 calculates the corrected $NO_x$ concentration Rno in accordance with Equation 1 with Equation 3 substituted into $\Delta NO$ of Equation 1.

In step S24 subsequent thereto, the microcomputer 60 outputs (transmits), as the "$NO_x$ concentration," the corrected $NO_x$ concentration Rno calculated in step S22 to the ECU 200 via the signal input/output section 64.

In step S26 subsequent thereto, the microcomputer 60 determines whether to end the pressure correction processing. In the case where the microcomputer 60 makes an "Yes" determination, it ends this processing. In the case where the microcomputer makes a "No" determination, it returns to step S8, and repeatedly executes steps S8 to S26 until it makes an "Yes" determination in step S26.

By means of executing the pressure correction processing as described above, the microcomputer 60 can correct the $NO_x$ concentration detected from the second pumping current Ip2 of the $NO_x$ sensor 100.

1-4. Comparative Measurements

In order to verify the effect of the correction performed by the $NO_x$ detection apparatus 10 of the present embodiment, measurements were performed by use of the $NO_x$ detection apparatus 10 and a conventional $NO_x$ detection apparatus, and the results of measurements were compared. The results of the measurements will be described below.

In a first comparative measurement, the concentration of $NO_x$ was measured in a state in which correction was performed by the method of the present embodiment and in a state in which correction was performed by the conventional method. In this first comparative measurement, the $NO_x$ concentration was set to 1500 ppm, and the pressure of the to-be-measured gas was changed.

Notably, the $NO_x$ concentration corrected by the conventional method refers to the $NO_x$ concentration corrected by use of only the above-described Equation 2. Namely, the $NO_x$ concentration corrected by the conventional method refers to the $NO_x$ concentration corrected without reflecting the effect of Equation 3 which is substituted into the above-described Equation 1.

Figure 6:
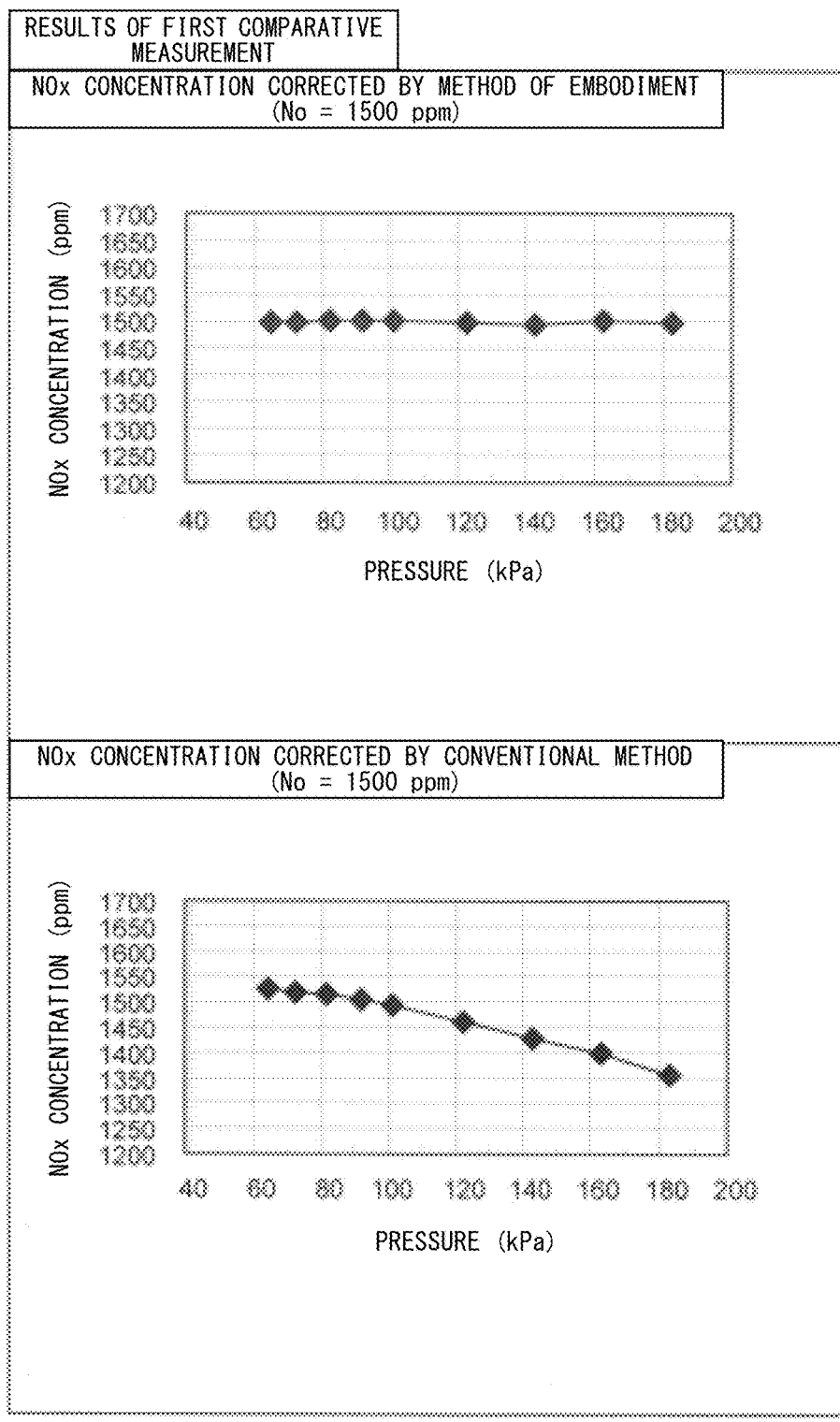
FIG. 6 consists of graphs showing the results of a first comparative measurement.

FIG. 6 shows the result of the first comparative measurement. As shown in FIG. 6, the $NO_x$ concentration corrected by the method of the present embodiment is nearly equal to the actual $NO_x$ concentration (1500 ppm) irrespective of a change in the pressure of the to-be-measured gas. This demonstrates that the $NO_x$ concentration can be detected with reduced influences of a change in the pressure of the to-be-measured gas.

Meanwhile, since the $NO_x$ concentration corrected by the conventional method differs little from the actual $NO_x$ concentration (1500 ppm) within a range where the pressure of the to-be-measured gas is between 60 and 120 kPa, the effect of correction is observed. However, within a range where the pressure of the to-be-measured gas exceeds 120 kPa, the difference from the actual $NO_x$ concentration increases with increasing pressure.

As seen from the above, the $NO_x$ detection apparatus 10 of the present invention can accurately detect gas even in the case where the pressure of the to-be-measured gas varies in a state in which the $NO_x$ concentration is 1500 ppm.

Figure 8:
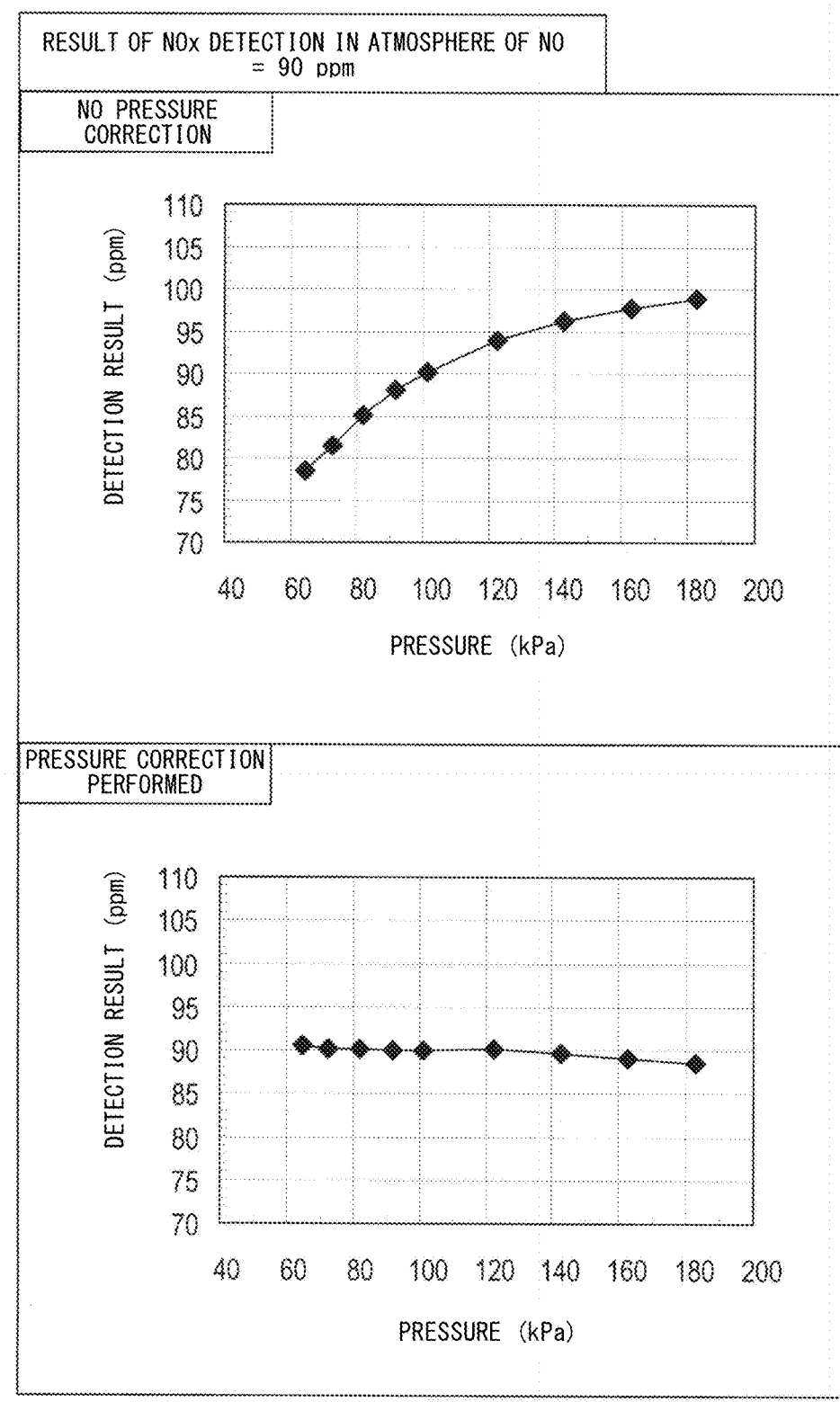
FIG. 8 consists of graphs showing the results of detection of $NO_x$ concentration by a conventional $NO_x$ detection apparatus when the $NO_x$ concentration is 90 ppm.
Figure 9:
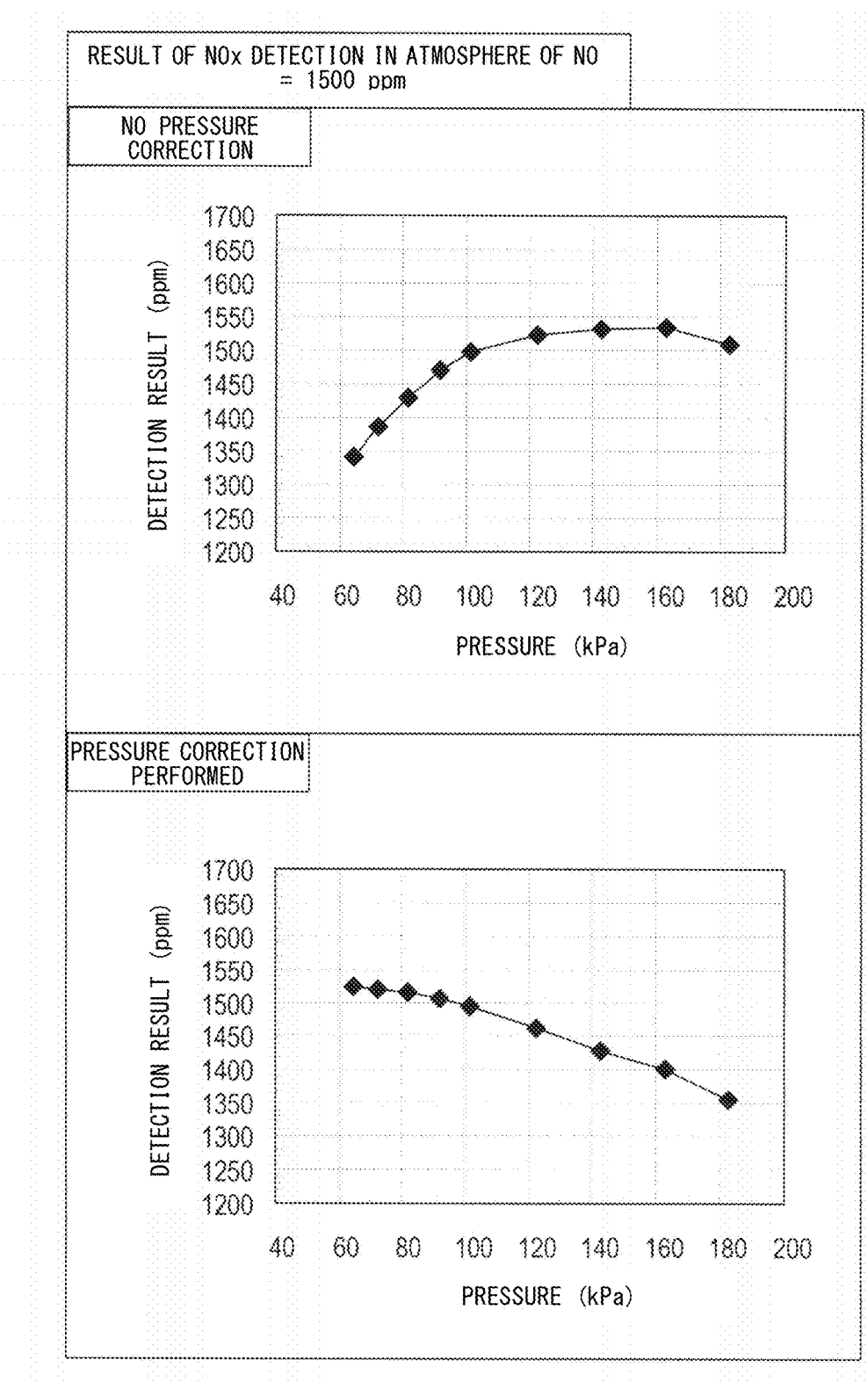
FIG. 9 consists of graphs showing the results of detection of $NO_x$ concentration by the conventional $NO_x$ detection apparatus when the $NO_x$ concentration is 1500 ppm.

Notably, when the $NO_x$ concentration is 90 ppm, the $NO_x$ detection apparatus 10 of the present embodiment provides a detection result similar to the detection result provided by the conventional $NO_x$ detection apparatus for the case where "pressure correction is performed" (see the graph on the lower side of FIG. 8). Accordingly, the result of detection of the $NO_x$ concentration by the $NO_x$ detection apparatus 10 of the present embodiment becomes approximately 90 ppm irrespective of a change in the pressure of the to-be-measured gas. In other words, even in the case where the $NO_x$ concentration is 90 ppm, the $NO_x$ detection apparatus 10 of the present embodiment can suppress the influence of a change in the pressure of the to-be-measured gas, to thereby suppress a decrease in gas detection accuracy.

That is, the $NO_x$ detection apparatus 10 of the present embodiment can detect the $NO_x$ concentration while suppressing the influence of the output variation caused by a change in the pressure of the to-be-measured gas in each of the case where the $NO_x$ concentration is 90 ppm and the case where the $NO_x$ concentration is 1500 ppm.

Next, in a second comparative measurement, a sensor output drop ratio obtained before correction by the above-described Equation 5 (correction equation for specific concentration range) and a sensor output drop ratio obtained after correction by the Equation 5 were measured in a state in which the $NO_x$ concentration was changed with the pressure of the to-be-measured gas maintained constant.

Notably, in the second comparative measurement, a gas containing NO (0-1500 ppm), $H_2O$ (4%), $O_2$ (7%), and $N_2$ (balance) was used as a sample gas. This measurement was conducted for fifty-five $NO_x$ sensors. Further, the sensor output drop ratio is calculated by use of the following method. First, the actual $NO_x$ concentration (hereinafter also referred to as the $NO_x$ actual concentration) is subtracted from the detected $NO_x$ concentration so as to calculate a difference value, and then the ratio [%] of the difference value to the $NO_x$ actual concentration is calculated as the sensor output drop ratio.

Figure 7:
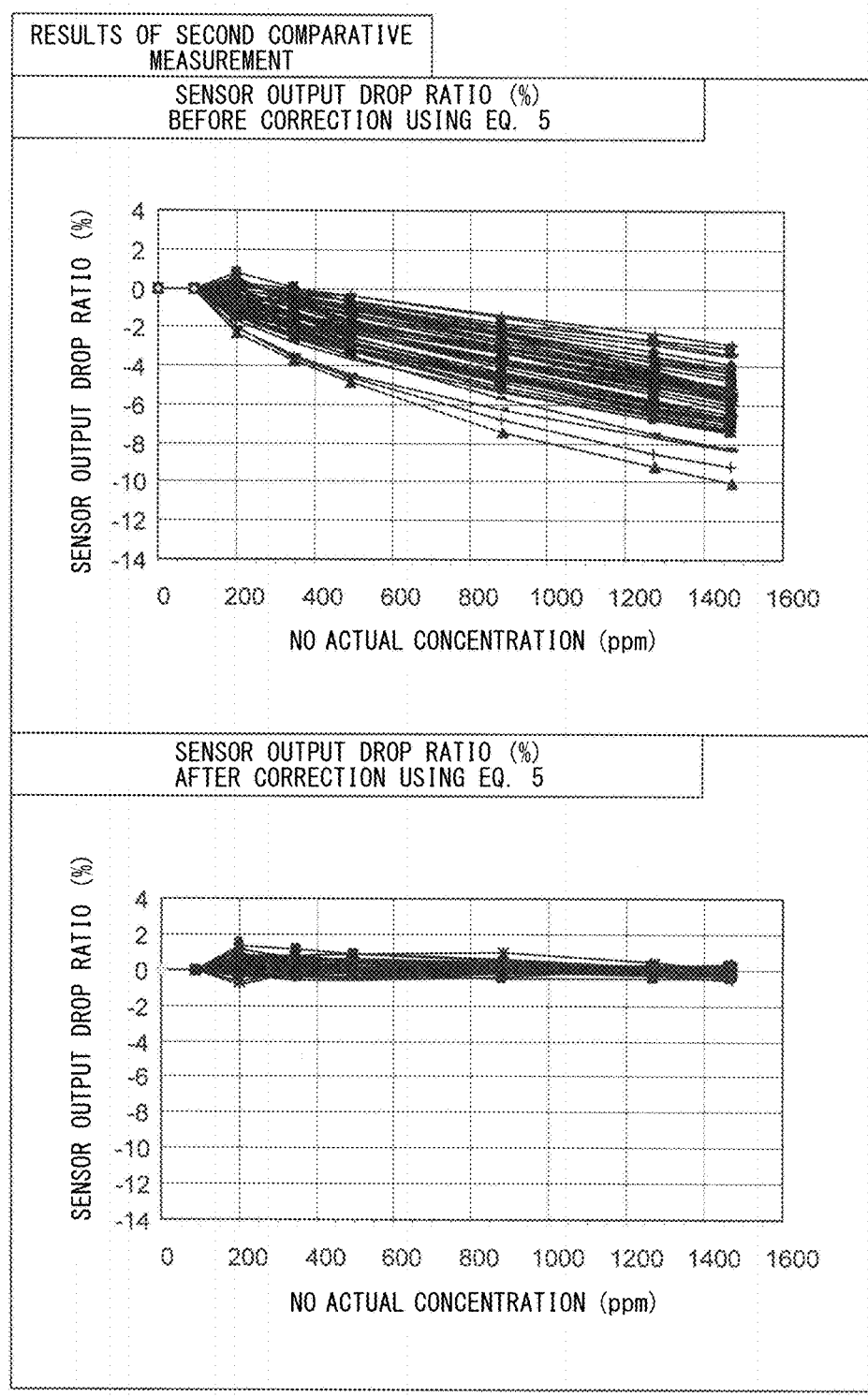
FIG. 7 consists of graphs showing the results of a second comparative measurement.

FIG. 7 shows results of the second comparative measurements. The graph on the upper side of FIG. 7 shows the sensor output drop ratios of the fifty-five $NO_x$ sensors before the correction by Equation 5. This graph shows that, in a range in which the $NO_x$ actual concentration is equal to or higher than 200 ppm, the absolute value of the sensor output drop ratio exceeds 0.2% in at least one of the $NO_x$ sensors. This graph also shows that the difference (error) between the detected $NO_x$ concentration and the $NO_x$ actual concentration increases with the $NO_x$ actual concentration.

The graph on the lower side of FIG. 7 shows the sensor output drop ratios of the fifty-five $NO_x$ sensors after the correction by Equation 5. This graph shows that the absolute value of the sensor output drop ratio becomes smaller than 0.2% in all the $NO_x$ sensors. This graph also shows that the difference (error) between the detected $NO_x$ concentration and the $NO_x$ actual concentration is small irrespective of the change in the $NO_x$ actual concentration.

As seen from the above, by means of performing correction by use of Equation 5, the difference between the detected $NO_x$ concentration and the $NO_x$ actual concentration can be rendered small even in the concentration range where the $NO_x$ actual concentration exceeds 200 ppm.

1-5. Effects

As described above, the $NO_x$ detection apparatus (or the $NO_x$ sensor system 1) of the present embodiment computes the second $NO_x$ concentration $NO_{xp}$ on the basis of the second pumping current Ip2 (step S12), obtains the first $NO_x$ concentration $NO_{xpo}$ by correcting the second $NO_x$ concentration $NO_{xp}$ (step S13), and sets the correction coefficients a and b (concentration variation correction information) by using the first $NO_x$ concentration $NO_{xpo}$ (steps S16 and S20). Therefore, the $NO_x$ detection apparatus 10 can set the correction coefficients a and b (concentration variation correction information) in accordance with the concentration of $NO_x$ actually contained in the to-be-measured gas.

In order to correct the first $NO_x$ concentration $NO_{xpo}$, the $NO_x$ detection apparatus 10 uses Equation 3 which is determined by the correction coefficients a and b (concentration variation correction information). Therefore, even in the case where the magnitude of an output variation caused by a change in pressure changes depending on the $NO_x$ concentration, the $NO_x$ detection apparatus 10 can correct the first $NO_x$ concentration $NO_{xpo}$ in accordance with the state of change of the concentration of $NO_x$ actually contained in the to-be-measured gas over the entire concentration range.

That is, by performing such correction, the $NO_x$ detection apparatus 10 can reduce the influence of an output variation caused by a change in the pressure of the to-be-measured gas over the entire concentration range.

Therefore, according to the $NO_x$ detection apparatus 10 of the present embodiment, even in the case where the magnitude of an output variation caused by a change in pressure changes depending on the $NO_x$ concentration, the influence of an output variation caused by a change in the pressure of the to-be-measured gas over the entire concentration range can be reduced, whereby a decrease in gas detection accuracy can be suppressed.

Also, in the present embodiment, a quadratic function (Equation 3) regarding the pressure P of the to-be-measured gas (to-be-measured gas pressure information) is used in Equation 1 for correcting the first $NO_x$ concentration $NO_{xpo}$. Therefore, the first $NO_x$ concentration $NO_{xpo}$ can be corrected in accordance with the state of change of the pressure of the to-be-measured gas. Also, since the coefficients (correction coefficients a and b) of the terms of the quadratic function of Equation 3 are set on the basis of the first $NO_x$ concentration $NO_{xpo}$ by the processing in step S16 or S20, these coefficients are changed in accordance with the concentration of $NO_x$ actually contained in the to-be-measured gas.

According to the $NO_x$ detection apparatus 10 of the present embodiment, correction is performed by using Equation 1. Therefore, even in the case where the magnitude of an output variation caused by a change in pressure changes depending on the $NO_x$ concentration, the influence of an output variation caused by a change in the pressure of the to-be-measured gas can be reduced, whereby a decrease in gas detection accuracy can be suppressed.

Also, in the present embodiment, the second $NO_x$ concentration $NO_{xp}$ is corrected on the basis of the pressure variation correction information ($k_1$), and the corrected second $NO_x$ concentration $NO_{xp}$ is used as the first $NO_x$ concentration $NO_{xpo}$. This enables the correction coefficients a and b (concentration variation correction information) to be set by using the first $NO_x$ concentration $NO_{xpo}$ in which the correction by the pressure variation correction information ($k_1$) is reflected. Therefore, the accuracy of the correction coefficients a and b (concentration variation correction information) increases, and a decrease in gas detection accuracy caused by a change in the pressure of the to-be-measured gas can be suppressed to a greater extent.

Also, when the first $NO_x$ concentration $NO_{xpo}$ computed on the basis of the second pumping current Ip2 falls within a concentration range of 90 ppm or higher (specific concentration range), the $NO_x$ detection apparatus 10 of the present embodiment corrects the first $NO_x$ concentration $NO_{xpo}$ by using the correction equation for specific concentration range represented by Equation 5. As a result, even in the case of use of an $NO_x$ sensor whose output involves an error in the concentration range of 90 ppm or higher (specific concentration range), the $NO_x$ detection apparatus 10 can detect the $NO_x$ concentration, while reducing the influence of the error of the sensor output, by correcting the first $NO_x$ concentration $NO_{xpo}$ by using the correction equation for specific concentration range represented by Equation 5.

Notably, the effect of the correction using the correction equation for specific concentration range represented by Equation 5 is shown by the results of the above-described second comparative measurement (FIG. 7).

In the case where the first $NO_x$ concentration $NO_{xpo}$ falls within the concentration range of 90 ppm or higher (specific concentration range) (a "Yes" determination is made in step S14), the $NO_x$ detection apparatus 10 corrects the first $NO_x$ concentration $NO_{xpo}$ by using the correction equation for specific concentration range represented by Equation 5 (step S18). In step S20 subsequent thereto, the $NO_x$ detection apparatus 10 computes the correction coefficients a and b on the basis of the first $NO_x$ concentration $NO_{xpo}$ ($NO_x$ concentration equivalent value) corrected in step S18.

Therefore, the $NO_x$ detection apparatus 10 can set the correction coefficients a and b while reducing the influence of the error of the sensor output. Thus, the $NO_x$ detection apparatus 10 can detect the $NO_x$ concentration while reducing the influence of the error of the sensor output.

Therefore, according to the present embodiment, even in the case where an $NO_x$ sensor whose output involves an error in the specific concentration range is used, it is possible to detect the $NO_x$ concentration while reducing the influence of the error of the sensor output. Further, even in the case where the magnitude of the output variation caused by a change in pressure changes depending on the $NO_x$ concentration, it is possible to reduce the influence of the output variation caused by a change in the pressure of the to-be-measured gas, to thereby suppress a decrease in gas detection accuracy.

1-6. Correspondence Relation Between Terms Appearing in the Description of the Present Embodiment and Terms Appearing in Claims Here, there will be described a correspondence relation between terms appearing in the description of the present embodiment and terms appearing in claims.

The inside first pumping electrode 113 and the outside first pumping electrode 112 correspond to an example of the "paired first electrodes," the inside second pumping electrode 133 and the counterpart second pumping electrode 132 correspond to an example of the "paired second electrodes," and the second measurement chamber 160 corresponds to an example of the $NO_x$ measurement chamber.

The microcomputer 60 which executes step S12 and S13 in the embodiment corresponds to an example of the first concentration calculation means, the microcomputer 60 which executes step S16 or S20 corresponds to an example of the correction information setting means, and the microcomputer 60 which executes step S22 corresponds to an example of the corrective computation means.

The $NO_x$ pressure correction coefficient ($k_1$) corresponds to an example of the pressure variation correction information, the pressure P of the to-be-measured gas corresponds to an example of the to-be-measured gas pressure information, and the correction coefficients a and b correspond to an example of the concentration variation correction information.

The microcomputer 60 which executes step S14 corresponds to an example of the specific concentration determination means, the microcomputer 60 which executes step S18 corresponds to an example of the first concentration correction means, and Equation 5 corresponds to an example of the specific concentration correction information.

2. Other Embodiments

The embodiment of the present invention has been described above. However, the present invention is not limited to the above-described embodiment, and various modifications are possible without departing from the scope of the present invention.

For example, in the above-described embodiment, a "concentration range of 90 ppm or higher" is set as a specific concentration range used in step S14. However, the specific concentration range used in step S14 is not limited to this range, and an arbitrary concentration range may be set in accordance with the characteristic of the $NO_x$ sensor, the measurement environment, or the like.

The method for correcting the $NO_x$ concentration in step S22 is not limited to a method of correcting the $NO_x$ concentration by using functions such as Equations 1 to 3, and another method for correcting the $NO_x$ concentration (e.g., a method for correcting the $NO_x$ concentration by using a map in which a correction amount is assigned to each of pressure ranges) may be used.

The map data sets used for computing the coefficients a and b in steps S16 and S20 are not limited to those shown in FIG. 4, and arbitrary map data sets may be used in accordance with the characteristic of the $NO_x$ sensor, the measurement environment, or the like. Similarly, the map data sets used for computing coefficients $\alpha$, $\beta$, and $\gamma$ in step S18 are not limited to those shown in FIG. 5, and arbitrary map data sets may be used in accordance with the characteristic of the $NO_x$ sensor, the measurement environment, or the like.

Meanwhile, in the present embodiment, in step S13, the first $NO_x$ concentration $NO_{xpo}$ ($NO_x$ concentration after pressure correction at pressure Po) is calculated by use of the second $NO_x$ concentration ($NO_x$ concentration before pressure correction) and Equation 2, and then the calculated result is output. Further, in step S22, the corrected $NO_x$ concentration Rno is calculated by use of Equation 1. However, the processing for calculating the corrected $NO_x$ concentration Rno is not limited to the above-described processing. For example, step S13 may be omitted. In this case, steps S14 to S20 are executed with the second $NO_x$ concentration $NO_{xp}$ ($NO_x$ concentration before pressure correction) used as the first $NO_x$ concentration, and the corrected $NO_x$ concentration Rno is then calculated by use of Equation 1 into which Equations 2 and 3 has been substituted.

DESCRIPTION OF REFERENCE NUMERALS

10: $NO_x$ sensor control apparatus ($No_x$ detection apparatus)
60: microcomputer
100: $No_x$ sensor
101: $No_x$ sensor element
110: first pumping cell
111: first solid electrolyte layer
112: outside first pumping electrode
113: inside first pumping electrode
120: oxygen concentration detection cell
121: second solid electrolyte layer
122: detection electrode
123: reference electrode
130: second pumping cell
131: third solid electrolyte layer
132: counterpart second pumping electrode
133: inside second pumping electrode
150: first measurement chamber
151: first diffusion resistor
152: second diffusion resistor
160: second measurement chamber
164: heater
170: reference oxygen chamber
300: pressure sensor

What is claimed is:
1. An $NO_x$ detection apparatus connected to an $NO_x$ sensor and adapted to detect an $NO_x$ concentration within a to-be-measured gas, the $NO_x$ sensor including a first measurement chamber, a first pumping cell including paired first electrodes positioned internally and externally, respectively, of the first measurement chamber, the first pumping cell pumping out oxygen from the to-be-measured gas introduced into the first measurement chamber and pumping oxygen into the first measurement chamber to adjust a concentration of oxygen within the first measurement chamber, an $NO_x$ measurement chamber in communication with the first measurement chamber, and a second pumping cell including paired second electrodes positioned internally and externally, respectively, of the $NO_x$ measurement chamber, a second pumping current flowing between the paired second electrodes and corresponding to the $NO_x$ concentration within the to-be-measured gas whose oxygen concentration has been adjusted in the first measurement chamber, the $NO_x$ sensor having predetermined specific concentration correction information set in advance,
the $NO_x$ detection apparatus comprising:
first concentration computation means for computing a first $NO_x$ concentration on the basis of the second pumping current;
correction information setting means for setting, using the first $NO_x$ concentration, concentration variation correction information for determining a degree of correction of the first $NO_x$ concentration;
corrective computation means for receiving, via an external input, to-be-measured gas pressure information, and for calculating the $NO_x$ concentration by correcting the first $NO_x$ concentration on the basis of the concentration variation correction information and the to-be-measured gas pressure information;
specific concentration determination means for determining whether the first $NO_x$ concentration falls within a predetermined specific concentration range; and
first concentration correction means for correcting the first $NO_x$ concentration using the predetermined specific concentration correction information, wherein
when the specific concentration determination means determines that the first $NO_x$ concentration falls within the predetermined specific concentration range, the correction information setting means sets the concentration variation correction information on the basis of the first $NO_x$ concentration as corrected by the first concentration correction means, and
when the specific concentration determination means determines that the first $NO_x$ concentration does not fall within the predetermined specific concentration range, the correction information setting means sets the concentration variation correction information on the basis of the first $NO_x$ concentration, which is not corrected by the first concentration correction means.

2. The $NO_x$ detection apparatus according to claim 1, wherein
the corrective computation means corrects the first $NO_x$ concentration using an n-th order function regarding the to-be-measured gas pressure information,
the n-th order function is a quadratic function or a higher-order function, and
the concentration variation correction information represents coefficients of terms of the n-th order function.

3. The $NO_x$ detection apparatus according to claim 1, wherein the first concentration computation means computes a second $NO_x$ concentration on the basis of the second pumping current, and obtains the first $NO_x$ concentration by correcting the second $NO_x$ concentration on the basis of predetermined pressure variation correction information which is individually set for each of $NO_x$ sensors in advance.

4. An $NO_x$ sensor system comprising:
an $NO_x$ sensor including a first measurement chamber, a first pumping cell including paired first electrodes positioned internally and externally, respectively, of the first measurement chamber, the first pumping cell pumping out oxygen from a to-be-measured gas introduced into the first measurement chamber and pumping oxygen into the first measurement chamber to adjust a concentration of oxygen within the first measurement chamber, an $NO_x$ measurement chamber in communication with the first measurement chamber, and a second pumping cell including paired second electrodes positioned internally and externally, respectively, of the $NO_x$ measurement chamber, a second pumping current flowing between the paired second electrodes and corresponding to an $NO_x$ concentration within the to-be-measured gas whose oxygen concentration has been adjusted in the first measurement chamber; and
an $NO_x$ detection apparatus according to claim 1, the $NO_x$ detection apparatus connected to the $NO_x$ sensor and adapted to detect the $NO_x$ concentration within the to-be-measured gas.

* * * * *